United States Patent
Snow

(10) Patent No.: US 11,920,120 B2
(45) Date of Patent: Mar. 5, 2024

(54) INTEGRATED CONTINUOUS ISOLATION OF FLUID STREAMS FROM STERILE PROCESS VESSELS

(71) Applicant: Genzyme Corporation, Cambridge, MA (US)

(72) Inventor: Robert Snow, Southborough, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 17/456,504

(22) Filed: Nov. 24, 2021

(65) Prior Publication Data

US 2022/0081669 A1 Mar. 17, 2022

Related U.S. Application Data

(60) Division of application No. 17/027,017, filed on Sep. 21, 2020, which is a continuation of application No. 14/918,107, filed on Oct. 20, 2015, now abandoned.

(60) Provisional application No. 62/068,181, filed on Oct. 24, 2014.

(51) Int. Cl.
| | |
|---|---|
| C12M 1/12 | (2006.01) |
| C12M 1/00 | (2006.01) |
| C12M 1/26 | (2006.01) |
| C12P 21/00 | (2006.01) |

(52) U.S. Cl.
CPC ............ *C12M 37/00* (2013.01); *C12M 23/58* (2013.01); *C12M 29/04* (2013.01); *C12M 29/10* (2013.01); *C12M 29/26* (2013.01); *C12M 33/04* (2013.01); *C12M 37/02* (2013.01); *C12M 37/06* (2013.01); *C12P 21/00* (2013.01)

(58) Field of Classification Search
CPC .............. A61L 2202/14; C12M 1/121; C12M 37/00; C12M 23/58; C12M 29/04; C12M 29/10; C12M 29/26; C12M 33/04; C12M 37/02; C12M 37/06; C12M 1/00; C12M 1/12; C12M 1/26; C12P 21/00
See application file for complete search history.

(56) References Cited

U.S. PATENT DOCUMENTS

| | | | |
|---|---|---|---|
| 5,409,841 | A | 4/1995 | Show |
| 5,626,767 | A | 5/1997 | Trampler et al. |
| 6,085,602 | A | 7/2000 | Schorn et al. |
| 6,664,095 | B1 | 12/2003 | Suryanarayan et al. |
| 9,650,412 | B2 | 5/2017 | Konstantinov et al. |
| 9,650,413 | B2 | 5/2017 | Konstantinov et al. |
| 9,657,056 | B2 | 5/2017 | Konstantinov et al. |
| 2004/0204379 | A1 | 10/2004 | Cheng et al. |
| 2007/0131615 | A1 | 6/2007 | Moran et al. |
| 2007/0249030 | A1* | 10/2007 | Fahrenthold ............... C12P 7/08 435/161 |
| 2009/0166300 | A1 | 7/2009 | Osborn et al. |
| 2010/0081122 | A1 | 4/2010 | Shibuya et al. |
| 2010/0151558 | A1 | 6/2010 | Alianell et al. |
| 2012/0164066 | A1 | 6/2012 | Greene et al. |
| 2013/0143313 | A1 | 6/2013 | Niazi |
| 2013/0164796 | A1 | 6/2013 | Licamele et al. |
| 2013/0164824 | A1 | 6/2013 | Licamele et al. |
| 2014/0120605 | A1* | 5/2014 | Wolters ..................... B65B 1/04 53/425 |
| 2014/0123777 | A1 | 5/2014 | Newbold et al. |
| 2014/0154726 | A1 | 6/2014 | Yang et al. |
| 2014/0255994 | A1 | 9/2014 | Konstantinov et al. |
| 2014/0295532 | A1 | 10/2014 | Ray et al. |
| 2015/0158907 | A1 | 6/2015 | Konstantinov et al. |
| 2016/0115438 | A1 | 4/2016 | Snow |
| 2017/0218012 | A1 | 8/2017 | Konstantinov et al. |

FOREIGN PATENT DOCUMENTS

| | | |
|---|---|---|
| CN | 1157634 | 8/1997 |
| CN | 1807599 | 7/2006 |
| CN | 101182465 | 5/2008 |
| CN | 101200691 | 6/2008 |
| CN | 102459560 | 5/2012 |
| CN | 203513669 | 4/2014 |
| CN | 112206847 | 1/2021 |
| DE | 9421778 | 11/1996 |
| EP | 1498475 | 1/2005 |
| JP | S63-123377 | 8/1988 |
| JP | H07-505071 | 6/1995 |
| JP | 4260877 | 4/2009 |
| RU | 102618 | 3/2011 |
| RU | 109275 | 10/2011 |

(Continued)

OTHER PUBLICATIONS

EPA (1999; Wastewater technology fact sheet ozone disinfection. Epa 832-F-99-063, on the web at www3.epa.gov/npdes/pubs/ozon.pdf, pp. 1-7.*
Boegger Industech Limited (downloaded 2022; Packed tower-working principle and advantages in industrial filtering, on the web at www.demisterpads.com/demister-pad/packed-tower.html, pp. 1-4.*
U.S. Appl. No. 61/878,502, filed Sep. 16, 2013, Zhou et al.
Australian Office Action in Patent Application No. 2015336130, dated Nov. 13, 2019, 8 pages.
Brazilian Office Action in Patent Application No. BR112017008252-7, dated Aug. 3, 2021, 10 pages (with English translation).
Brazilian Office Action in Patent Application No. BR112017008252-7, dated Nov. 12, 2019, 9 pages.

(Continued)

*Primary Examiner* — Iqbal H Chowdhury
(74) *Attorney, Agent, or Firm* — Fish & Richardson P.C.

(57) ABSTRACT

Provided herein are isolation processes and the associated hardware to allow fluid streams to be isolated from a sterilized system (e.g., a sterile process vessel) that contains a sterile process. The isolation processes described herein allow for continuous removal of fluid streams (e.g., waste streams, liquid containing recombinant therapeutic proteins) from a sterilized system (e.g., a biological manufacturing system), which provides for less manual manipulation of the sterilized system and a decreased risk of contaminating the sterilized system.

8 Claims, 2 Drawing Sheets

(56) References Cited

FOREIGN PATENT DOCUMENTS

| TW | M283863 | 12/2005 |
| TW | I691342 | 4/2020 |
| WO | WO 1993/17724 | 9/1993 |
| WO | WO 1996/008556 | 3/1996 |
| WO | WO 2011/038008 | 3/2011 |
| WO | WO 2013/096682 | 6/2013 |
| WO | WO 2014/004281 | 1/2014 |
| WO | WO 2014/137903 | 9/2014 |

OTHER PUBLICATIONS

Canadian Office Action in Patent Application No. 2,965,478, dated Sep. 21, 2021, 4 pages.
Chinese Office Action in Patent Application No. 201580070285.9, dated Feb. 3, 2019, 22 pages.
Chinese Office Action in Patent Application No. 201580070285.9, dated Jan. 8, 2021, 7 pages.
Chinese Office Action in Patent Application No. 201580070285.9, dated May 27, 2020, 9 pages.
European Communication in Patent Application No. 15791822.8, dated May 8, 2018, 4 pages.
Gebauer et al., "Engineered protein scaffolds as next-generation antibody therapeutics," Current Opin. Chem. Biol., 2009, 13(3):245-255.
Indian Office Action in Patent Application No. 201737017730, dated Dec. 30, 2020, 9 pages.
Israel Office Action in Patent Application No. 251819, dated May 23, 2019, 9 pages.
Japanese Office Action in Patent Application No. 2017-522117, dated Jul. 23, 2019, 7 pages.
Japanese Office Action in Patent Application No. 2020-035426, dated Apr. 6, 2021, 7 pages.
PCT International Preliminary Report on Patentability in International Appln. No. PCT/US2015/056422, dated Apr. 25, 2017, 6 pages.
PCT International Search Report and Written Opinion in International Appln. No. PCT/US2015/056422, dated Apr. 4, 2016, 11 pages.
Russian Office Action in Patent Application No. 2017115655, dated Apr. 17, 2019, 7 pages.
Russian Office Action in Patent Application No. 2017115655, dated Aug. 7, 2019, 19 pages.
Russian Office Action in Patent Application No. 2017115655, dated Jul. 15, 2019, 6 pages (with English translation).
Russian Office Action in Patent Application No. 2017115655, dated Nov. 25, 2019, 15 pages (with English translation).
Singapore Examination Report in Application No. 11201703265X, dated Jan. 12, 2018, 4 pages.
Taiwan Office Action in Patent Application No. 104134623, dated Dec. 16, 2019, 2 pages (with English translation).
Taiwan Office Action in Patent Application No. 104134623, dated Jan. 10, 2019, 3 pages (with English translation).
Taiwan Office Action in Patent Application No. 104134623, dated Jul. 17, 2019, 1 page (with English translation).
Taiwan Office Action in Patent Application No. 109108985, dated Aug. 27, 2020, 8 page (with English translation).
Taiwan Office Action in Patent Application No. 109108985, dated May 18, 2021, 9 pages (with English translation).
Office Action in Korean Patent Application No. 10-2017-7013748, dated Feb. 9, 2022, 15 pages (with English translation).
Written Opinion in Singapore Patent Application No. 10201801943S, dated Jun. 22, 2022, 9 pages.
Office Action in Chinese Patent Application No. 202110310605.0, dated Jun. 16, 2023, 12 pages (with English translation).
Written Opinion in Singapore Patent Application No. 10201801943S, dated Aug. 18, 2023, 9 pages.
Russian Office Action in Patent Application No. 2020102925, dated Feb. 16, 2022, 16 pages (with English translation).

* cited by examiner

INTEGRATED CONTINUOUS ISOLATION OF FLUID STREAMS FROM STERILE PROCESS VESSELS

PRIORITY

This application is a divisional of U.S. patent application Ser. No. 17/027,017, filed Sep. 21, 2020, which is a continuation of U.S. patent application Ser. No. 14/918,107, filed Oct. 20, 2015 (now abandoned), which claims the benefit of U.S. Provisional Patent Application Ser. No. 62/068,181, filed on Oct. 24, 2014, the entirety of each of which is incorporated herein by reference.

TECHNICAL FIELD

This invention relates to methods of biotechnology and the biomanufacturing of recombinant proteins.

BACKGROUND

Mammalian cells containing a nucleic acid that encodes a recombinant protein are often used to produce therapeutically or commercially important proteins. In the current environment of diverse product pipelines, biotechnology companies are increasingly driven to develop innovative solutions for highly flexible and cost-effective manufacturing of therapeutic agents (e.g., therapeutic protein drug substances).

In a continuous biomanufacturing process, it is often necessary to remove fluids from a sterile process vessel. The removal of such fluid may either be a continuous flow or an intermittent flow based on some predefined trigger. The removal needs to be done in such a way as to protect the sterility of the vessel that the fluid is being removed from. This can be challenging in biomanufacturing when the fluid stream has the potential to promote biological growth which can eventually grow back to the sterile process vessel. The predominant method used today is a batch transfer method, where the waste streams are collected in a second sterile vessel and when that vessel reaches capacity it is then disconnected from the sterile process vessel and the waste is then discarded. This is not ideal as it is a batch process (not continuous) and there is a lot of time involved in the handling and sterilizing of the vessels. These manipulations also create process risk if any step should fail. Alternatively the same process can be accomplished with presterilized bags, however the cost of the bags can be prohibitive for a continuous process and the use of bags does not eliminate the process risk.

SUMMARY

The present invention is based, in part, on the development of an isolation process and the associated hardware to allow fluid streams to be periodically or continuously isolated (e.g., removed) from a sterilized system (e.g., a sterile process vessel) that contains a sterile process. The isolation process utilizes an isolation vessel to separate the sterile process from the environment and waste streams. The isolation vessel is only partially filled and maintains a head space within the vessel, wherein the head space contains a sterilizing agent. The sterilizing agent (e.g., a sterilizing gas (e.g., a gas containing ozone, ethylene oxide, nitrogen dioxide, or vaporized hydrogen peroxide)) can be sparged into the vessel or introduced directly into the head space of the vessel. The sterilizing agent maintains a sterilizing atmosphere within the head space of the vessel, which provides isolation between the incoming sterile process stream and the outgoing fluid stream (e.g., a waste stream). The concentration of the sterilizing agent (e.g., a sterilizing gas) is controlled within the headspace of the vessel to provide the necessary sterilizing atmosphere.

In one aspect, the disclosure provides a method of inhibiting contamination of a sterilized system, the method comprising providing a system comprising first vessel, wherein the first vessel comprises a liquid, flowing a first volume of the liquid out of the first vessel and through a volume of sterilizing gas and into a second vessel. The sterilized systems contemplated herein include, but are not limited to, biological manufacturing systems and pharmaceutical manufacturing systems. The first vessel is a sterilized vessel. In exemplary embodiments, the first vessel comprises a component of a biological manufacturing system. For example, the first vessel can be a (e.g., any of the exemplary bioreactors described herein or known in the art), one or more components of chromatography systems (e.g., a chromatography column), one or more components of microfiltration system, or one or more components of an ultrafiltration/diafiltration (UF/DF) system. For a biological manufacturing system, the liquid of the first vessel can be a liquid culture medium and/or a liquid comprising a recombinant therapeutic protein. In some embodiments, the liquid of the first vessel comprises a cell comprising a recombinant therapeutic protein. The recombinant therapeutic protein can be a protein secreted from the cell or not secreted from the cell.

In some aspects, the sterilizing gas is selected from the group consisting of ozone, ethylene oxide, nitrogen dioxide, vaporized hydrogen peroxide (e.g., an ozone containing gas, an ethylene oxide containing gas, a nitrogen oxide containing gas, and a hydrogen dioxide containing gas).

The first volume of liquid flowed from the first vessel to the second vessel can be a waste stream. In another aspect, the first volume of liquid flowed from the first vessel to the second vessel comprises a recombinant therapeutic protein. Alternatively, the first volume of liquid flowed from the first vessel to the second vessel does not contain a recombinant therapeutic protein (i.e., the first volume of liquid is a waste stream or comprises culture media prior to initiation of the cell culture). The first volume of liquid may comprise fermentation by-products.

In one aspect, the methods disclosed herein further comprise flowing a second volume of liquid from the second vessel into an apparatus for purifying and polishing a recombinant protein. For example, the method disclosed herein may further comprise flowing a second volume of liquid from the second vessel into a first multi-column chromatography system (MCCS1), capturing said recombinant therapeutic protein in the liquid culture medium using the MCCS1, wherein the eluate of the MCCS1 containing the recombinant therapeutic protein is continuously fed into a second multi-column chromatography system (MCCS2), and purifying and polishing the recombinant therapeutic protein using the MCCS2, wherein the eluate from the MCCS2 is a recombinant therapeutic protein; and wherein the process is integrated and runs continuously from said liquid in the first vessel to the eluate from the MCCS2 that is the recombinant therapeutic protein. In some embodiments, the second volume of liquid comprises a recombinant protein.

In one aspect, the methods disclosed herein further comprise flowing a second volume of liquid from the second vessel into a receptacle for disposing of a biological waste stream. The receptacle can be, for example, a sink for disposing waste, or a beaker or other container for storing and/or removing the waste liquid.

The disclosure also provides a system for isolating sterile process streams from non-sterile environments. In one aspect, the system comprises a first vessel comprising a fluid outlet; and at least one second vessel comprising a fluid inlet in fluid communication with the fluid outlet of the first vessel and configured such that fluid entering the second vessel passes through a sterilizing-gas filled head space within the second vessel, a fluid outlet configured such that fluid exiting second vessel is removed from below the sterilizing gas-filled headspace within the second vessel, at least one gas inlet, and at least one gas outlet. In some examples, the first vessel is a sterilized vessel. In an exemplary embodiment, the first vessel is a component of a biological manufacturing system. For example, the first vessel is a fluid conduit (e.g., any of the exemplary bioreactors described herein or known in the art), one or more components of chromatography systems (e.g., a chromatography column), one or more components of microfiltration system, or one or more components of an ultrafiltration/diafiltration system. The bioreactor is, for example, a perfusion bioreactor, a fed-batch seed bioreactor, production bioreactor, or a seed bioreactor. In some embodiments, the second vessel fluid outlet is in fluid communication with an apparatus for purifying and polishing a recombinant protein. In an exemplary embodiment, the first vessel and the second vessel are disposed on a skid.

In some aspects, the systems disclosed herein further comprise a fluid conduit disposed between the first vessel and the second vessel, and, optionally, further comprises a filter disposed in the fluid conduit between the first vessel and the second vessel and configured to remove particulate matter from the fluid in the fluid conduit. The systems disclosed herein can also include a pump system (e.g., a pump), where the pump system is disposed in a fluid conduit. In some examples, the systems disclosed herein comprise a pump in fluid communication with the fluid outlet of the first vessel, a pump in fluid communication with a fluid outlet of the section vessel, or both. In one embodiment, the pump system is configured to remove a volume of fluid from the vessel outlet and flow the volume into the fluid inlet of the second vessel.

In one aspect, the systems disclosed herein comprised a sterilizing gas-filled head space within the second vessel. The sterilizing gas can be, for example, a gas selected from the group consisting of ozone, ethylene oxide, nitrogen dioxide, or vaporized hydrogen peroxide. In some embodiments, the at least one gas inlet is connected to one or more gas sparging elements which permit gas to be emitted into the second vessel and supplied to the head space. The term "sparging element" refers is a porous element (e.g., a filter, an open pipe or a frit) for bubbling a gas through a liquid. To fill the headspace, the second vessel comprises at least one gas inlet in gas communication with a system for generating or delivering a sterilizing gas, or for generating and delivering a sterilizing gas. In some embodiments, the system for generating or delivering a sterilizing gas is an ozone generation or delivery system, or an ozone generation and delivery system. In some embodiments, the system for delivering a sterilizing gas is bottled gas. Also, in some embodiments, the second vessel comprises at least one gas outlet configured to continuously or periodically vent gas from the second vessel. For systems using ozone, the gas outlet is in gas communication with an ozone destruction unit. To control the concentration or amount of sterilizing gas contained the second vessel the system can include, for example, a dissolved gas probe or a sensor for monitoring the sterilizing gas concentration within the headspace of the second vessel.

In one aspect, the first vessel comprises a fluid outlet in fluid communication with a fluid inlet of the second vessel. In an exemplary embodiment, the second vessel comprises a fluid inlet configured such that the volume of liquid entering the second vessel passes through the head space (e.g., a fluid inlet located on the second vessel in a position above the liquid level), a fluid outlet configured such that liquid exiting the second vessel is flowed from below the sterilizing gas-filled headspace (e.g., a fluid outlet located on the second vessel in a position below the liquid level), at least one gas inlet, and at least one gas outlet, wherein the fluid inlet is in fluid communication with the first vessel. Advantageously, the volume of sterilizing gas is disposed within a headspace of the second vessel. To fill the headspace, the sterilizing gas can be sparged into the second vessel or introduced directly into the head space of the second vessel. In some examples, the second vessel is at least partially filed with a liquid.

In some embodiments, the liquid in the first vessel comprises a recombinant therapeutic protein.

As used herein, the word "a" before a noun represents one or more of the particular noun. For example, the phrase "a recombinant mammalian cell" represents "one or more recombinant mammalian cells."

The term "vessel" is art known and means a device (e.g., a container), of any shape or size, having an interior volume suitable for containing a volume of liquid or gas. The vessel can be open (i.e., a device that interacts directly with its external environment) or closed (i.e., an isolated device that has no interaction with its external environment). The term "vessel" includes, for example, a device having an interior volume suitable for culturing a plurality of cells (e.g., recombinant mammalian cells) in a liquid culture medium under a controlled set of physical conditions that allow for the maintenance or proliferation of the cells. Non-limiting examples of vessels are fluid conduits, bioreactors (e.g., any of the exemplary bioreactors described herein or known in the art), one or more components of chromatography systems (e.g., a chromatography column), one or more components of microfiltration system, one or more components of an ultrafiltration/diafiltration system, beakers, sinks, or tubes.

The term "sterilization" is art-known and refers to any validated process used to render a composition sterile, e.g., a process that eliminates (removes) or kills all forms of life, including transmissible agents (such as fungi, bacteria, viruses, spore forms, etc.) present on a surface, contained in a fluid, in a medication, or in a compound such as biological culture media. Sterilization can be achieved by applying heat, chemicals (e.g. a gas), irradiation, high pressure, or filtration or combinations thereof.

The term "sterilizing gas" as used herein refers a gas or gaseous composition capable of rendering a composition sterile, e.g., a process that eliminates (removes) or kills all forms of life, including transmissible agents (such as fungi, bacteria, viruses, spore forms, etc.) present on a surface, contained in a fluid, in medication, or in a compound such as biological culture media.

"Absolute sterility" or "absolutely sterile" are terms used to describe a composition or process that is/are completely free of self-replicating biological contaminants. For example, the term can apply to a gamma-irradiated vessel, the interior surface and contents of a vessel, and/or a buffer.

An absolutely sterile composition or process can be clean (as that term is known in the art).

"Sterile" or "sterility" are terms used to describe a composition or process that have a sterility assurance level of about or less than $1.0 \times 10^{-6}$ (e.g., about or less than $1.0 \times 10^{-7}$, about or less than $1.0 \times 10^{-8}$, about or less than $1.0 \times 10^{-9}$, or $1 \times 10^{-10}$). The determination of whether a composition or process is sterile can be tested using a number of validated production processes known in the art. For example, a sterile composition or process can be completely free of viable self-replicating biological contaminants (e.g., any of the self-replicating biological contaminants described herein). A sterile composition or process can also be clean (as that term is known in the art). A sterile cell culture is free of contamination.

The term "sterility assurance level" or "SAL" is art-known and means a level of confidence of achieving absolute sterility within a batch of treated units. The probability is usually calculated based on the results of inactivation studies performed during validation and expressed in the form of $1 \times 10^{-n}$.

The terms "sterilized vessel" and "sterile process vessel" are interchangeable and refer to a vessel which has been subjected to a sterilization process. As used herein, the term "sterilized vessel" or "sterile process vessel" include, for example, a vessel containing bioburden controlled monoculture (e.g., a bioburden controlled monoculture of recombinant mammalian cells). As used herein, the term "sterilized system" refers to a system comprising collection of one or more (e.g., two, three, four, five, six, seven, eight, nine, ten or more) sterile process vessels that function cooperatively to achieve a specific result (e.g., the expression and purification of a recombinant protein from a liquid culture medium). A "sterilized system" refers to a system of a total of two or more interconnected or switching vessels wherein at least one or more of the vessels of the system is a sterilized vessel.

As used herein, the term "biological manufacturing system" or "biomanufacturing system" refers to system for producing a biological drug. The term "pharmaceutical manufacturing system" refers to system for producing a small molecule drug (e.g., a drug, prodrug or a drug product). Components of biological manufacturing systems and pharmaceutical systems contemplated herein, include, for example, one or more bioreactors for culture initiation and production, flasks, fluid conduits, vessels one or more components of chromatography systems (e.g., a chromatography column, pumps, process vessels), one or more components of a filtration system (e.g., a one or more components of a microfiltration system, or one or more components of an ultrafiltration/diafiltration system) and other devices utilized for drug isolation and purification. The systems may be open, closed, integrated or continuous as defined herein or as otherwise the generally understood by one skilled in the art.

The term "biological drug", as used herein, refers to any therapeutic substance made or obtained from a living organism or its products that is used in the prevention, diagnosis or treatment of a pathology. Thus, a biological drug or biopharmaceutical is a medical drug produced using biotechnology, for example, a protein (e.g., a recombinant therapeutic protien), or a nucleic acid (DNA, RNA or antisense oligonucleotides), used for therapeutic or in vivo diagnostic purposes.

The term "small molecule drug," as used herein, refers to a therapeutic agent having low molecular weight that is used in the prevention, diagnosis or treatment of a pathology. The therapeutic agent is usually synthesized by organic chemistry, but may also be isolated from natural sources such as plants, fungi, and microbes.

As used herein, a first vessel is in "gas communication" with a second vessel when the first and second vessels are connected via device or conduit allowing for gas flow or communication between the vessels. Similarly, a first vessel is in "fluid communication" with a second vessel when the first and second vessels are connected via device or conduit allowing for fluid flow or communication between the vessels. Consistent with the teachings of the present invention, the terms fluid communication and gas communication are intended to be synonymous terms. In this regard, a fluid is intended to include a substance, whether a liquid or a gas, tending to flow or conform to the outline of its container. In this respect, not only does a liquid conform to the definition of fluid, but a gas also does because a gas can flow and conforms to the outline of the container within which it resides.

The term "perfusion bioreactor" is art-known and means a bioreactor having an interior volume for culturing a plurality of cells (e.g., recombinant mammalian cells) in a liquid culture medium, and having a means (e.g., an outlet, an inlet, a pump, or other such device) for periodically or continuously removing the liquid culture medium in the bioreactor and having a means (e.g., an outlet, an inlet, a pump, or other such device) for adding substantially the same volume of a replacement liquid culture medium to the bioreactor. The adding of the replacement liquid culture medium can perform at substantially the same time or shortly after the removing the liquid culture medium from the bioreactor. The means for removing the liquid culture medium from the bioreactor and the means for adding the replacement liquid culture medium can be a single device or system.

The term "production bioreactor" is a term of art and means a large-scale bioreactor (e.g., having an internal volume over 500 L, 1,000 L, 5,000 L, 10,000 L, 20,000 L, 50,000 L, or 100,000 L). For example, a production bioreactor can be a perfusion bioreactor.

The term "fed-batch bioreactor" is a term of art and means a bioreactor including a plurality of cells (e.g., recombinant mammalian cells) in a first liquid culture medium, wherein the culturing of the cells present in the bioreactor includes the periodic or continuous addition of a second liquid culture medium to the first liquid culture medium without substantial or significant removal of the first liquid culture medium or second liquid culture medium from the cell culture. The second liquid culture medium can be the same as the first liquid culture medium. In some examples of fed-batch culture, the second liquid culture medium is a concentrated form of the first liquid culture medium. In some examples of fed-batch culture, the second liquid culture medium is added as a dry powder.

The term "multi-column chromatography system" or "MCCS" means a system of a total of two or more interconnected or switching chromatography columns and/or chromatographic membranes. A non-limiting example of a multi-column chromatography system is a periodic counter current chromatography system (PCC) including a total of two or more interconnected or switching chromatography columns and/or chromatographic membranes. Additional examples of multi-column chromatography systems are described herein and are known in the art.

The term "mammalian cell" means any cell from or derived from any mammal (e.g., a human, a hamster, a mouse, a green monkey, a rat, a pig, a cow, or a rabbit). For example, a mammalian cell can be an immortalized cell. In some embodiments, the mammalian cell is a differentiated cell. In some embodiments, the mammalian cell is an undifferentiated cell. Non-limiting examples of mammalian cells are described herein. Additional examples of mammalian cells are known in the art.

The term "culturing" or "cell culturing" means the maintenance or proliferation of a mammalian cell (e.g., a recombinant mammalian cell) under a controlled set of physical conditions.

The term "culture of mammalian cells" or "cell culture" means a liquid culture medium containing a plurality of mammalian cells that is maintained or proliferated under a controlled set of physical conditions.

The term "liquid culture medium" or "culture medium" means a fluid that contains sufficient nutrients to allow a cell (e.g., a mammalian cell) to grow or proliferate in vitro. For example, a liquid culture medium can contain one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, and sodium bicarbonate. In some embodiments, a liquid culture medium can contain serum from a mammal. In some embodiments, a liquid culture medium does not contain serum or another extract from a mammal (a defined liquid culture medium). In some embodiments, a liquid culture medium can contain trace metals, a mammalian growth hormone, and/or a mammalian growth factor. Another example of liquid culture medium is minimal medium (e.g., a medium containing only inorganic salts, a carbon source, and water). Non-limiting examples of liquid culture medium are described herein. Additional examples of liquid culture medium are known in the art and are commercially available. A liquid culture medium can contain any density of mammalian cells. For example, as used herein, a volume of liquid culture medium removed from a production bioreactor can be substantially free of mammalian cells.

The term "recombinant therapeutic protein" or "recombinant protein" is art known and means includes any therapeutic protein obtained via recombinant DNA technology. As used herein, a "recombinant therapeutic protein" includes, for example, an antibody or antibody fragment, an enzyme, an engineered protein, or an immunogenic protein or protein fragment.

The term "protein fragment" or "polypeptide fragment" means a portion of a polypeptide sequence that is at least or about 4 amino acids, at least or about 5 amino acids, at least or about 6 amino acids, at least or about 7 amino acids, at least or about 8 amino acids, at least or about 9 amino acids, at least or about 10 amino acids, at least or about 11 amino acids, at least or about 12 amino acids, at least or about 13 amino acids, at least or about 14 amino acids, at least or about 15 amino acids, at least or about 16 amino acids, at least or about 17 amino acids, at least or about 18 amino acids, at least or about 19 amino acids, or at least or about 20 amino acids in length, or more than 20 amino acids in length. A recombinant protein fragment can be produced using any of the processes described herein.

The term "engineered protein" means a polypeptide that is not naturally encoded by an endogenous nucleic acid present within an organism (e.g., a mammal). Examples of engineered proteins include enzymes (e.g., with one or more amino acid substitutions, deletions, insertions, or additions that result in an increase in stability and/or catalytic activity of the engineered enzyme), fusion proteins, antibodies (e.g., divalent antibodies, trivalent antibodies, or a diabody), and antigen-binding proteins that contain at least one recombinant scaffolding sequence.

The term "integrated process" means a process which is performed using structural elements that function cooperatively to achieve a specific result (e.g., the generation of an isolated recombinant protein from a liquid culture medium).

The term "continuous process" means a process which continuously feeds fluid through at least a part of the system.

The term "filtering" means the removal of at least part of (e.g., at least 80%, 90%, 95%, 96%, 97%, 98%, or 99%) undesired biological contaminants (e.g., a mammalian cell, bacteria, yeast cells, viruses, or mycobacteria) and/or particulate matter (e.g., precipitated proteins) from a liquid (e.g., a liquid culture medium or fluid present in any of the systems or processes described herein).

The term "perfusion culturing" is a term of art and means the culturing of a cell culture in a vessel (e.g., a bioreactor), wherein the culturing of the cell culture in the vessel includes the periodic or continuous removal of liquid culture medium present in the vessel (e.g., liquid culture medium that is substantially fee of cells) and at the same time or shortly thereafter adding substantially the same volume of a replacement liquid culture medium to the vessel. In some examples, there is an incremental change (e.g., increase or decrease) in the volume of liquid culture medium removed and the volume of replacement culture medium added over incremental periods (e.g., an about 24-hour period, a period of between about 1 minute and about 24-hours, or a period of greater than 24 hours) during the culturing period (e.g., the culture medium refeed rate on a daily basis). The fraction of media removed and replaced each day can vary depending on the particular cells being cultured, the initial seeding density, and the cell density at a particular time. "RV" or "reactor volume" means the volume of the culture medium present at the beginning of the culturing process (e.g., the total volume of the culture medium present after seeding).

The term "fed-batch culturing" is a term of art and means a vessel (e.g., a production bioreactor) including a plurality of cells (e.g., mammalian cells) in a liquid culture medium, wherein the culturing of the cells present in the vessel (e.g., production bioreactor) includes the periodic or continuous addition of fresh liquid culture medium to the vessel without substantial or significant removal of liquid culture medium from the vessel during culturing. The fresh liquid culture medium can be the same as the liquid culture medium present in the vessel at the start of the culturing. In some examples of fed-batch culturing, the fresh liquid culture medium is a concentrated form of the liquid culture medium present in the vessel at the start of culturing. In some examples of fed-batch culture, the fresh culture medium is added as a dry powder.

"Skid" is a term of art and as used herein refers to a three-dimensional solid structure that can act as a platform or support for a system described herein. A skid can, if it comprises one or more structures that enable movement (e.g., wheels, rollers, or the like), confer mobility on the system or a portion thereof. Non-limiting examples of skids are described herein. Additional examples of skids are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used.

The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
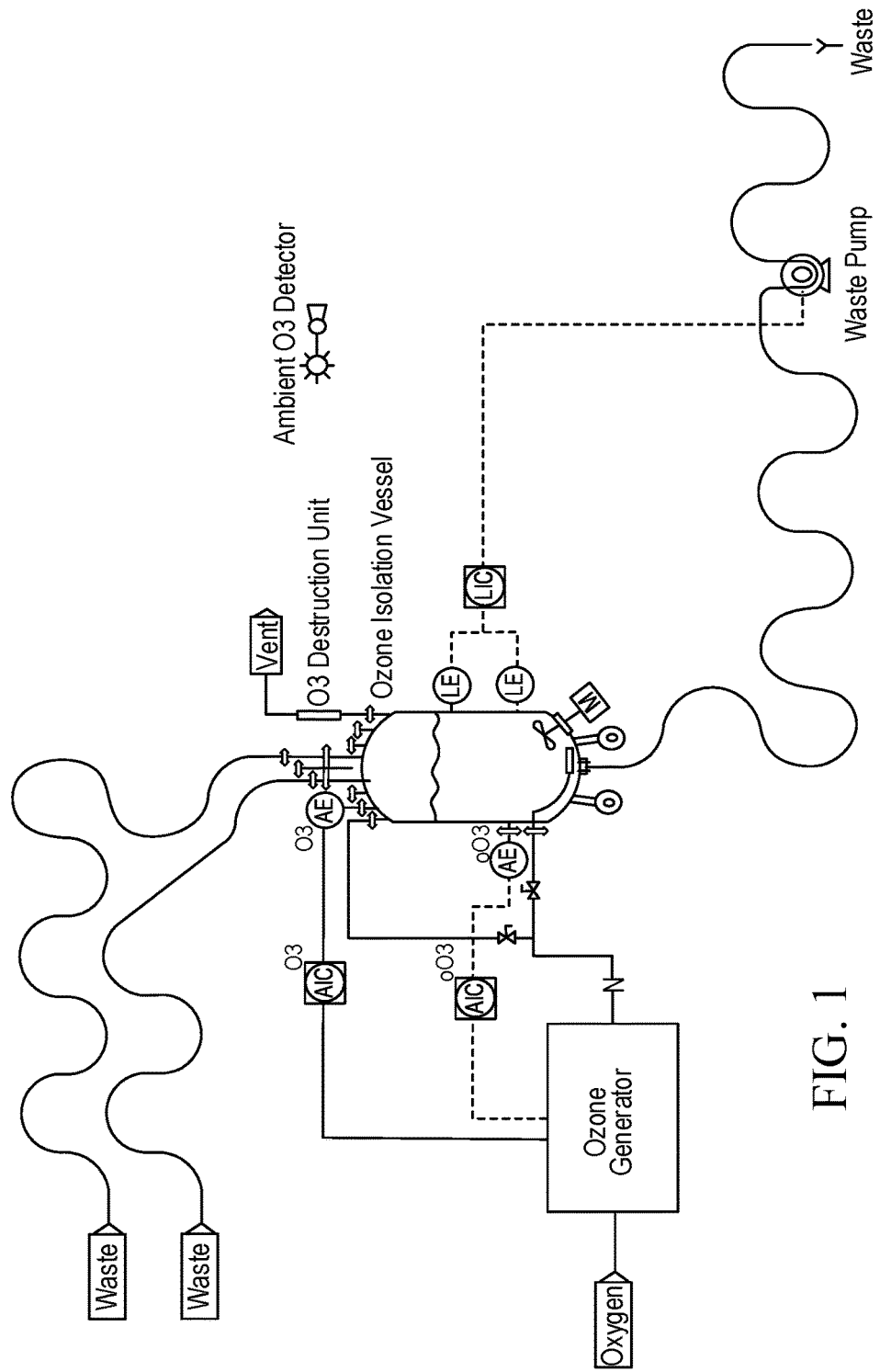
FIG. 1 is a schematic diagram illustrating an example system for isolating sterile process streams from non-sterile environments according to the present invention.

Provided herein are isolation processes and the associated hardware to allow fluid streams to be isolated from a sterilized system (e.g., a sterile process vessel) that contains a sterile process. The isolation processes described herein provide for many benefits. For instance, the isolation processes allow for periodic or continuous removal of fluid streams from a sterilized system, which provides for less manual manipulation of the sterilized system and a decreased risk of contaminating the sterilized system. For example, the isolation processes described herein provide for periodic or continuous removal of liquid (e.g., waste streams, liquid containing recombinant therapeutic proteins) from a bioreactor, which in turn provides for less manual manipulation of the cell culture and a decreased risk of contaminating the cell culture. Non-limiting aspects of these isolation processes are described herein, and can be used in any combination.

The methods described herein comprise flowing fluid volumes from a first vessel to a second vessel, flowing fluid volumes from a third vessel to a forth vessel, or flowing fluid volumes from a fifth vessel to a sixth vessel. As can be appreciated in the art, there are many ways to flow volume of liquid from a first vessel to a second vessel, such as gravity flow or with the aid of a pump. Thus, in some aspects, the systems described herein can also include one or more (e.g., two, three, four, or five) pumps (e.g., automated, e.g., automated peristaltic pumps). The one or more pumps can be disposed in fluid conduit disposed between a first vessel and a second vessel. For example, the systems described herein can also include one or more pumps configured to remove a volume of fluid from a first vessel outlet and flow the volume to a second vessel. In some examples the one or more pumps configured to remove a volume of fluid from a sterile process vessel outlet and flow the volume into the isolation vessel fluid inlet as described herein. In some examples, one or more pumps are in fluid communication with the at least one fluid outlet of the isolation vessel. The fluid can be removed from the sterile process vessel can be removed by a pump system (e.g., an alternating tangential flow (ATF) filtration system or tangential fluid filtration (TFF)).

In some examples, the systems described herein can also include one or more (e.g., two, three, four, or five) filters for removing undesired biological contaminants (e.g., a mammalian cell, bacteria, yeast cells, viruses, or mycobacteria) and/or particulate matter (e.g., precipitated proteins) from a liquid (e.g., a liquid culture medium or fluid present in any of the systems or processes described herein).

In some aspects, the disclosure provides methods of inhibiting contamination of a sterilized system comprising providing a system comprising first vessel, wherein the first vessel comprises a liquid, flowing a first volume of the liquid out of the first vessel and through a volume of sterilizing gas and into a second vessel.

In some aspects, the disclosure provides methods of inhibiting contamination of a sterilized system comprising providing a system comprising a first vessel, wherein the first vessel comprises a liquid, flowing a first volume of the liquid out of the first vessel and through a volume of sterilizing gas and into a second vessel. In some examples, the first vessel is a sterile process vessel, wherein the sterile process vessel comprises a fluid outlet in fluid communication with a fluid inlet of the second vessel. In some examples, the second vessel is an isolation vessel as described herein, and the volume of sterilizing gas is disposed within the head space of the isolation vessel.

In some aspects, the disclosure provides systems for isolating sterile process streams from non-sterile environments. For some examples, the system comprises a sterile process vessel (e.g., a first vessel) comprising a fluid outlet, and at least one isolation vessel (e.g., a second vessel), the at least one isolation vessel comprising (i) a fluid inlet in fluid communication with the fluid outlet of the first vessel and configured such that fluid entering the second vessel passes through a sterilizing-gas filled head space within the second vessel, (ii) a fluid outlet configured such that fluid exiting second vessel is removed from below the sterilizing gas-filled headspace within the second vessel, (iii) at least one gas inlet; and (iv) at least one gas outlet. In some examples, the systems disclosed herein further comprise a fluid conduit disposed between the first vessel and the second vessel.

The isolation processes disclosed herein utilize a vessel (i.e., an "isolation vessel") to separate the sterile process from the environment and waste streams. In some examples, the isolation vessel comprises (i) a fluid inlet in fluid communication with the fluid outlet of a sterile process vessel and configured such that fluid entering the isolation vessel passes through a sterilizing-gas filled head space within the isolation vessel, (ii) a fluid outlet configured such that fluid exiting isolation vessel is removed from below the sterilizing gas-filled headspace within the isolation vessel, (iii) at least one gas inlet; and (iv) at least one gas outlet.

As can be appreciated in the art, the isolation vessel can have a variety of different volumes. For example, the isolation vessel can have an internal volume of between about 0.20 L to about 20 L (e.g., between about 0.20 L and about 18 L, between about 0.20 L and about 16 L, between about 0.20 L and about 14 L, between about 0.20 L and about 12 L, between about 0.20 L and about 10 L, between about 0.20 L and about 9.0 L, between about 0.20 L and about 8.0 L, between about 0.20 L and about 7.0 L, between about 0.20 L and about 6.0 L, between about 0.20 L and about 5.0 L, between about 0.20 L and about 4.0 L, between about 0.20 L and about 3.0 L, between about 0.20 L and about 2.0 L, between about 0.20 L and about 1.0 L, between about 0.50 L and about 18 L, between about 0.50 L and about 16 L, between about 0.50 L and about 14 L, between about 0.50 L and about 12 L, between about 0.50 L and about 10 L, between about 0.50 L and about 9.0 L, between about 0.50 L and about 8.0 L, between about 0.50 L and about 7.0 L, between about 0.50 L and about 6.0 L, between about 0.50 L and about 5.0 L, between about 0.50 L and about 4.0 L, between about 0.50 L and about 3.0 L, between about 0.50 L and about 2.0 L, between about 0.50 L and about 1.0 L, between about 1.0 L to about 20 L, between about 1.0 L and about 18 L, between about 1.0 L and about 16 L, between about 1.0 L and about 14 L, between about 1.0 L and about 12 L, between about 1.0 L and about 10 L, between about 1.0 L and about 9.0 L, between about 1.0 L and about 8.0 L, between about 1.0 L and about 7.0 L, between about 1.0 L and about 6.0 L, between about 1.0 L and about 5.0 L, between about 1.0 L and about 4.0 L, between about 1.0 L and about 3.0 L, between about 1.0 L and about 2.0 L, between about 1.0 L and about 1.0 L), or about 0.20 L, about 0.50 L, about 1.0 L, about 2.0 L, about 3.0 L, about 4.0 L, about 5.0 L, about 6.0 L, about 7.0 L, about 8.0 L, about 9.0 L, about 10.0 L, about 12.0 L, about 14.0 L, about 16.0 L, about 18.0 L or about 20.0 L.

The isolation vessel is only partially filled and maintains a head space within the vessel. The head space can include sterilizing agent (e.g., a sterilizing gas). In some examples, the sterilizing-gas filled head space contained within the isolation vessel occupies between about 3% to about 97% of the total interior volume of the isolation vessel; between about 5% to about 95% of the total interior volume of the isolation vessel, e.g., between about 10% to about 90% of the total interior volume of the isolation vessel; between about 15% to about 85% of the total interior volume of the isolation vessel; between about 20% to about 80% of the total interior volume of the isolation vessel; between about 25% to about 75% of the total interior volume of the isolation vessel; between about 30% to about 70% of the total interior volume of the isolation vessel; between about 35% to about 65% of the total interior volume of the isolation vessel; between about 40% to about 60% of the total interior volume of the isolation vessel; between about 45% to about 55% of the total interior volume of the isolation vessel; or about 5% of the total interior volume of the isolation vessel; about 10% of the total interior volume of the isolation vessel; about 15% of the total interior volume of the isolation vessel, about 20% of the total interior volume of the isolation vessel; about 25% of the total interior volume of the isolation vessel; about 30% of the total interior volume of the isolation vessel; about 35% of the total interior volume of the isolation vessel; about 40% of the total interior volume of the isolation vessel; about 45% of the total interior volume of the isolation vessel; about 50% of the total interior volume of the isolation vessel; about 55% of the total interior volume of the isolation vessel; about 60% of the total interior volume of the isolation vessel; about 65% of the total interior volume of the isolation vessel; about 75% of the total interior volume of the isolation vessel; about 80% of the total interior volume of the isolation vessel; about 85% of the total interior volume of the isolation vessel; about 90% of the total interior volume of the isolation vessel; or about 95% of the total interior volume of the isolation vessel.

Exemplary sterilizing gases for use in the systems and methods disclosed herein include, for example, ozone gas, ethylene oxide gas, nitrogen dioxide gas and vaporized hydrogen dioxide (e.g., an ozone containing gas, an ethylene oxide containing gas, a nitrogen oxide containing gas, and a hydrogen dioxide containing gas), or any appropriate mixture of such gases. In some examples, the sterilizing gas contained within the head space of the isolation vessel can be maintained, for example, at a temperature of between about 15° C. and about 70° C., about 20° C. and about 65° C., about 25° C. and about 60° C., about 30° C. and about 55° C., about 35° C. and about 50° C., or about 40° C. and about 45° C.

Ozone offers many advantages as a sterilizing gas. Ozone is a very efficient sterilizing agent because of its strong oxidizing properties, which are capable of destroying a wide range of pathogens, including prions. The high reactivity of ozone means that waste ozone can be destroyed by passing the ozone over a simple catalyst that reverts the ozone to oxygen. It also means that the cycle time is relatively short. In some examples, the head space contains ozone, e.g., an ozone containing gas having an ozone concentration of at least about 3000 ppm, e.g., at least about 4000 ppm, at least about 5000 ppm, at least about 6000 ppm, at least about 7000 ppm, at least about 8000 ppm, at least about 9000 ppm, at least about 10,000 ppm, at least about 15,000 ppm, at least about 20,000 ppm, at least about 50,000 ppm, at least about 100,000 ppm, at least about 500,000 ppm or at least about 1,000,000 ppm.

Ethylene oxide has microbiocidal properties and can kill all known viruses, bacteria and fungi, including bacterial spores and is compatible with most materials (e.g. sterile process vessels used in biological manufacturing processes). In some examples, the head space contains ethylene oxide, e.g., an ethylene oxide containing gas having an ethylene oxide concentration of at least about 500 ppm, e.g., at least about 850 ppm, at least about 1000 ppm, at least about 2000 ppm, at least about 3000 ppm, at least about 4000 ppm, at least about 5000 ppm, at least about 6,000 ppm, at least about 7,000 ppm, at least about 8,000 ppm, at least about 9,000 ppm, at least about 10,000 ppm, at least about 15,000 ppm, at least about 20,000 ppm, at least about 50,000 ppm, at least about 100,000 ppm, at least about 500,000 ppm or at least about 1,000,000 ppm.

Nitrogen Dioxide ($NO_2$) gas is effective as a sterilant against a wide range of microorganisms, including common bacteria, viruses, and spores. In some examples, the head space contains nitrogen dioxide, e.g., an nitrogen dioxide containing gas having an ethylene oxide concentration of at least about 500 ppm, at least about 850 ppm, at least about 1000 ppm, at least about 2000 ppm, at least about 3000 ppm, at least about 4000 ppm, at least about 5000 ppm, at least about 6,000 ppm, at least about 7,000 ppm, at least about 8,000 ppm, at least about 9,000 ppm, at least about 10,000 ppm, at least about 15,000 ppm, at least about 20,000 ppm, at least about 50,000 ppm, at least about 100,000 ppm, at least about 500,000 ppm or at least about 1,000,000 ppm.

Hydrogen peroxide ($H_2O_2$) has good sterilizing properties and can be decomposed to water and oxygen. In some examples, the head space contains hydrogen peroxide, e.g., a hydrogen peroxide containing gas having an ethylene oxide concentration of at least about 5 ppm, at least about 5 ppm, at least about 10 ppm, at least about 50 ppm, at least about 100 ppm, at least about 250 ppm, at least about 500 ppm, at least about 850 ppm, at least about 1000 ppm, at least about 2000 ppm, at least about 3000 ppm, at least about 4000 ppm, at least about 5000 ppm, at least about 6,000 ppm, at least about 7,000 ppm, at least about 8,000 ppm, at least about 9,000 ppm, at least about 10,000 ppm, at least about 15,000 ppm, at least about 20,000 ppm, at least about 50,000 ppm, at least about 100,000 ppm, at least about 500,000 ppm or at least about 1,000,000 ppm.

The isolation vessel may further include a component for monitoring the concentration of the sterilizing agent (e.g., a sterilizing gas) within the headspace of the vessel to monitor the sterilizing atmosphere. For example, an isolation vessel can include a sensor for monitoring the sterilizing gas concentration within the headspace, or a sensor (e.g., a dissolved gas probe) for monitoring the dissolved gas concentration of the liquid contained in isolation vessel.

In some examples, the liquid filled space within the isolation vessel represents between about 3% to about 97% of the total volume of the isolation vessel; between about 5% to about 95% of the total volume of the isolation vessel; between about 10% to about 90% of the total volume of the isolation vessel; between about 15% to about 85% of the total volume of the isolation vessel; between about 20% to about 80% of the total volume of the isolation vessel; between about 25% to about 75% of the total volume of the isolation vessel; between about 30% to about 70% of the total volume of the isolation vessel; between about 35% to about 65% of the total volume of the isolation vessel; between about 40% to about 60% of the total volume of the isolation vessel; between about 45% to about 55% of the total volume of the isolation vessel; or about 5% of the total volume of the isolation vessel; about 10% of the total volume of the isolation vessel; about 15% of the total volume of the isolation vessel, about 20% of the total volume of the isolation vessel; about 25% of the total volume of the isolation vessel; about 30% of the total volume of the isolation vessel; about 35% of the total volume of the isolation vessel; about 40% of the total volume of the isolation vessel; about 45% of the total volume of the isolation vessel; about 50% of the total volume of the isolation vessel; about 55% of the total volume of the isolation vessel; about 60% of the total volume of the isolation vessel; about 65% of the total volume of the isolation vessel; about 75% of the total volume of the isolation vessel; about 80% of the total volume of the isolation vessel; about 85% of the total volume of the isolation vessel; about 90% of the total volume of the isolation vessel; or about 95% of the total volume of the isolation vessel.

An isolation vessel can include at least one gas inlet for introducing a sterilizing gas into the head space of the isolation vessel. As can be appreciated in the art, there are many ways that a gas may be introduced to the head space of a vessel. For example, the gas may be sparged into the vessel or introduced directly into the head space of the vessel. Thus, the at least one gas inlet can be connected to one or more gas sparging elements which permit gas to be emitted into the isolation vessel. The gas inlet can be in gas communication via a conduit with a system for generating or delivering a sterilizing gas, or for generating and delivering a sterilizing gas (e.g., ozone, ethylene oxide, nitrogen dioxide, or vaporized hydrogen peroxide). For example, the gas inlet can be in in gas communication with a system for generating ozone, as is well known in the art.

The isolation vessel can include at least one gas outlet configured to continuously or periodically vent gas from the head space of the isolation vessel. As can be appreciated in the art, the gas outlet can be configured to automatically vent gas, should the headspace gas pressure be excessive. The gas outlet can be in gas communication with a unit configured to contain, destroy or attenuate the sterilizing gas. For example, the gas outlet can be in in gas communication with an ozone destruction unit. Ozone destruction units are art-known and can be catalytic, thermal, thermo-catalytic or activated carbon. The catalytic units can use either manganese dioxide or aluminum coated with palladium and destroy ozone at temperatures around 50° C. Thermal destructive units typically operate at temperatures around 120° C.

In some examples, the isolation vessel described herein comprises at least one fluid inlet in fluid communication with at least one fluid outlet of a sterile process vessel and configured such that fluid entering the isolation vessel passes through a sterilizing-gas filled head space within the isolation vessel. In some aspects, the at least one fluid inlet of the isolation vessel is in fluid communication with the at least one fluid outlet of a sterile process vessel via a fluid conduit.

In some examples, the isolation vessel described herein comprises at least one fluid outlet. For some exemplary system configurations, the at least one fluid outlet of the isolation vessel is in fluid communication with an apparatus for purifying and polishing a recombinant protein. Thus, in some aspects, the methods disclosed herein comprise flowing a volume of liquid from the isolation vessel (e.g., the second vessel) into an apparatus for purifying and polishing a recombinant protein.

The term "purifying" means a step performed to isolate a recombinant protein (e.g., a recombinant therapeutic protein) from one or more other impurities (e.g., bulk impurities) or components present in a fluid containing a recombinant protein (e.g., liquid culture medium proteins or one or more other components (e.g., DNA, RNA, other proteins, endotoxins, viruses, etc.) present in or secreted from a mammalian cell). For example, purifying can be performed during or after an initial capturing step. Purification can be performed using any method known in the art, e.g., using a resin, membrane, or any other solid support that binds either a recombinant protein or contaminants (e.g., through the use of affinity chromatography, hydrophobic interaction chromatography, anion or cation exchange chromatography, or molecular sieve chromatography). A recombinant protein can be purified from a fluid containing the recombinant protein using at least one chromatography column and/or chromatographic membrane (e.g., any of the chromatography columns or chromatographic membranes described herein).

The term "polishing" is a term of art and means a step performed to remove remaining trace or small amounts of contaminants or impurities from a fluid containing a recombinant therapeutic protein that is close to a final desired purity. For example, polishing can be performed by passing a fluid containing the recombinant therapeutic protein through a chromatographic column(s) or membrane absorber(s) that selectively binds to either the target recombinant therapeutic protein or small amounts of contaminants or impurities present in a fluid containing a recombinant therapeutic protein. In such an example, the eluate/filtrate of the chromatographic column(s) or membrane absorber(s) contains the recombinant therapeutic protein.

For example, the disclosure provides methods comprising flowing a volume of liquid comprising a recombinant protein from the isolation vessel (e.g., the second vessel) into a first multi-column chromatography system (MCCS1), capturing said recombinant therapeutic protein in the liquid culture medium using the MCCS1, wherein the eluate of the MCCS1 containing the recombinant therapeutic protein is continuously fed into a second multi-column chromatography system (MCCS2); and purifying and polishing the recombinant therapeutic protein using the MCCS2, wherein the eluate from the MCCS2 is a recombinant therapeutic protein; and wherein the process is integrated and runs continuously from said first vessel to the eluate from the MCCS2 that is the recombinant therapeutic protein.

The term "multi-column chromatography system" or "MCCS" means a system of a total of two or more interconnected or switching chromatography columns and/or chromatographic membranes. A non-limiting example of a multi-column chromatography system is a periodic counter current chromatography system (PCC) containing a total of two or more interconnected or switching chromatography columns and/or chromatographic membranes. Additional examples of multi-column chromatography systems are described herein and are known in the art.

The term "capturing" means a step performed to partially purify or isolate (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight), concentrate, and stabilize a recombinant protein (e.g., a recombinant therapeutic protein) from one or more other components present in a liquid culture medium or a diluted liquid culture medium (e.g., culture medium proteins or one or more other components (e.g., DNA, RNA, or other proteins) present in or secreted from a mammalian cell). Typically, capturing is performed using a resin that binds a recombinant protein (e.g., through the use of affinity chromatography). Non-limiting methods for capturing a recombinant protein from a liquid culture medium or diluted liquid culture medium are described herein and others are known in the art. A recombinant protein can be captured from a liquid culture medium using at least one chromatography column and/or chromatographic membrane (e.g., any of the chromatography columns and/or chromatographic membranes described herein).

The term "eluate/filtrate" is a term of art and means a fluid that is emitted from a chromatography column or chromatographic membrane that contains a detectable amount of a recombinant protein (e.g., recombinant therapeutic protein).

The term "filtering" means the removal of at least part of (e.g., at least 80%, 90%, 95%, 96%, 97%, 98%, or 99%) undesired biological contaminants (e.g., a mammalian cell, bacteria, yeast cells, viruses, or mycobacteria) and/or particulate matter (e.g., precipitated proteins) from a liquid (e.g., a liquid culture medium or fluid present in any of the systems or processes described herein).

The term "secreted protein" or "secreted recombinant protein" means a protein (e.g., a recombinant protein) that originally contained at least one secretion signal sequence when it is translated within a mammalian cell, and through, at least in part, enzymatic cleavage of the secretion signal sequence in the mammalian cell, is secreted at least partially into the extracellular space (e.g., a liquid culture medium). Skilled practitioners will appreciate that a "secreted" protein need not dissociate entirely from the cell to be considered a secreted protein For some exemplary system configurations, the at least one fluid outlet fluid outlet of the isolation vessel is in fluid communication with a receptacle for accepting and/or disposing of waste material (e.g., a vessel, a sink, or a unit for disposing of biological process fluid material known to those of skill in the art).

The isolation processes and the systems allow fluid streams to be isolated from a vessel of a sterilized system (e.g., a sterile process vessel) that contains a sterile process. In some examples, the sterile process vessel contains a sterile process and comprises at least one fluid outlet for removing fluid from the vessel. For the processes and systems described herein, the at least one fluid outlet is in fluid communication with at least one fluid inlet of an isolation vessel, wherein the fluid inlet of the isolation vessel is configured such that fluid entering the isolation vessel passes through a sterilizing-gas filled head space within the isolation vessel.

As can be appreciated in the art, the sterile process vessel can have a variety of different volumes. For example, the sterile process vessel in step can have an internal volume of between about 0.50 L to about 200 L (e.g., between about 0.50 L and about 180 L, between about 0.50 L and about 160 L, between about 0.50 L and about 140 L, between about 0.50 L and about 120 L, between about 0.50 L and about 100 L, between about 0.50 L and about 90 L, between about 0.50 L and about 80 L, between about 0.50 L and about 70 L, between about 0.50 L and about 60 L, between about 0.50 L and about 50 L, between about 0.50 L and about 40 L, between about 0.50 L and about 30 L, between about 0.50 L and about 20 L, between about 0.50 L and about 10 L, between about 0.50 L and about 5.0 L, between about 1.0 L and about 200 L, between about 1.0 L and about 180 L, between about 1.0 L and about 160 L, between about 1.0 L and about 140 L, between about 1.0 L and about 120 L, between about 1.0 L and about 100 L, between about 1.0 L and about 90 L, between about 1.0 L and about 80 L, between about 1.0 L and about 70 L, between about 1.0 L and about 60 L, between about 1.0 L and about 50 L, between about 1.0 L and about 40 L, between about 1.0 L and about 30 L, between about 1.0 L and about 20 L, between about 1.0 L and about 10 L, between about 1.0 L and about 5.0 L, between about 1.5 L and about 200 L, between about 1.5 L and about 180 L, between about 1.5 L and about 160 L, between about 1.5 L and about 140 L, between about 1.5 L and about 120 L, between about 1.5 L and about 100 L, between about 1.5 L and about 90 L, between about 1.5 L and about 80 L, between about 1.5 L and about 70 L, between about 1.5 L and about 60 L, between about 1.5 L and about 50 L, between about 1.5 L and about 40 L, between about 1.5 L and about 30 L, between about 1.5 L and about 20 L, between about 1.5 L and about 10 L, between about 1.5 L and about 5.0 L, between about 2.0 L and about 200 L, between about 2.0 L and about 180 L, between about 2.0 L and about 160 L, between about 2.0 L and about 140 L, between about 2.0 L and about 120 L, between about 2.0 L and about 100 L, between about 2.0 L and about 90 L, between about 2.0 L and about 80 L, between about 2.0 L and about 70 L, between about 2.0 L and about 60 L, between about 2.0 L and about 50 L, between about 2.0 L and about 40 L, between about 2.0 L and about 30 L, between about 2.0 L and about 20 L, between about 2.0 L and about 10 L, between about 2.0 L and about 5.0 L, between about 2.5 L and about 200 L, between about 2.5 L and about 180 L, between about 2.5 L and about 160 L, between about 2.5 L and about 140 L, between about 2.5 L and about 120 L, between about 2.5 L and about 100 L, between about 2.5 L and about 90 L, between about 2.5 L and about 80 L, between about 2.5 L and about 70 L, between about 2.5 L and about 60 L, between about 2.5 L and about 50 L, between about 2.5 L and about 40 L, between about 2.5 L and about 30 L, between about 2.5 L and about 20 L, between about 2.5 L and about 10 L, between about 2.5 L and about 5.0 L, between about 5.0 L and about 200 L, between about 5.0 L and about 180 L, between about 5.0 L and about 160 L, between about 5.0 L and about 140 L, between about 5.0 L and about 120 L, between about 5.0 L and about 100 L, between about 5.0 L and about 90 L, between about 5.0 L and about 80 L, between about 5.0 L and about 70 L, between about 5.0 L and about 60 L, between about 5.0 L and about 50 L, between about 5.0 L and about 40 L, between about 5.0 L and about 30 L, between about 5.0 L and about 20 L, or between about 5.0 L and about 10 L).

In some examples, the vessel that contains the sterile process is a component of a biological manufacturing system. Components of biological manufacturing systems contemplated herein, include, for example, a flask, a fluid conduit, a bioreactor, one or more components of chromatography systems (e.g., a chromatography column), one or more components of microfiltration system, or one or more components of an ultrafiltration/diafiltration system.

In some embodiments, the bioreactor is a perfusion bioreactor, a fed-batch bioreactor, or a production bioreactor. The perfusion bioreactor can be any of the exemplary perfusion bioreactors described herein or known in the art. For example, a perfusion bioreactor can be made of stainless steel or plastic (e.g., a plastic sterile bag). The interior surface of a perfusion bioreactor may have at least one coating (e.g., at least one coating of gelatin, collagen, poly-L-ornithine, polystyrene, and laminin), and as is known in the art, one or more ports for the sparging of $O_2$, $CO_2$, and $N_2$ into the liquid culture medium, and a stir mechanism for agitating the liquid culture medium. The perfusion bioreactor can also be equipped with a mechanical device that is capable of removing a volume of fluid (e.g., liquid culture medium) from the bioreactor and optionally, a filter within the mechanical device that removes the cells from the fluid during the process of transfer of fluid out of the bioreactor (e.g., an alternating tangential flow (ATF), a tangential flow filtration (TFF) system, or a filtering system described in U.S. Provisional Patent Application No. 61/878,502). The bioreactor can also be equipped with one or more pumps, and one or more reservoirs to hold the removed fluid.

The volume of the liquid can be removed, e.g., using a mechanical system and/or by seeping or gravity flow of the volume through a sterile membrane with a molecular weight cut-off that excludes mammalian cells present in the volume.

As can be appreciated in the art, the vessel that contains the sterile process can be any apparatus used in the art for the purpose of culturing mammalian cells (e.g., a flask (e.g., a spin flask), a rolling tube, or a bioreactor). For example, the vessel that contains the sterile process can be any apparatus used in the art for the purpose of culturing recombinant mammalian cells. The vessel can include an internal means for agitation (e.g., an impeller) or the vessel can be agitated externally (e.g., through the use of a rotating and/or tilting platform). The vessel can be made of stainless steel or plastic (e.g., a plastic sterile bag). In some embodiments, the vessel can be a disposable single-use bioreactor (e.g., a 3-L polycarbonate disposable bioreactor (Millipore™ Mobius® Cellready 3 L disposable bioreactor), TK8 bioprocess film disposable 50-L bioreactor (Pierre Guerin ATM1 Nucleo™ 20 L disposable bioreactor), a multilayer film 50-L disposable bioreactor (Sartorius Cultibag SR™ 50 L disposable bioreactor), a multilayer film 20-L disposable bioreactor (Sartorius Cultibag RM™ 20 L), a multilayer film 50-L disposable bioreactor (Sartorius Cultibag Orbital™ 50 L), GE Wave Bioreactor 2/10 System 5 L, GE Wave Bioreactor 20/50 System 25 L, GE Wave Bioreactor 200 System 200 L, or GE Wave Bioreactor 500/1000 System 500 L). The interior surface of the vessel may have at least one coating (e.g., at least one coating of gelatin, collagen, poly-L-ornithine, polystyrene, and laminin), and as is known in the art, one or more ports for the sparging of $O_2$, $CO_2$, and $N_2$ into the first liquid culture medium. The vessel can be equipped with one or more sensor probe(s). When the vessel is composed of a non-rigid plastic material (e.g., a plastic sterile bag), the vessel can be connected to an exterior support that surrounds and supports the vessel.

A recombinant mammalian cell can be a human, mouse, hamster, or monkey cell. For example, a recombinant mammalian cell can be a cell line, e.g., Chinese hamster ovary (CHO) cells (e.g., CHO DG44 cells, CHO-K1s cells, C02.31 clonal cells, A14.13 clonal cells, C02.57 clonal cells, and F05.43 clonal cells), Sp2.0, myeloma cells (e.g., NS/0), B-cells, hybridoma cells, T-cells, human embryonic kidney (HEK) cells (e.g, HEK 293E and HEK 293F), African green monkey kidney epithelial cells (Vero) cells, or Madin-Darby Canine (Cocker Spaniel) kidney epithelial cells (MDCK) cells.

A nucleic acid encoding a recombinant protein can be introduced into a mammalian cell to produce a recombinant mammalian cell using a wide variety of methods known in molecular biology and molecular genetics. Non-limiting examples include transfection (e.g., lipofection), transduction (e.g., lentivirus, adenovirus, or retrovirus infection), and electroporation. In some instances, the nucleic acid that encodes a recombinant protein is not stably integrated into a chromosome of the recombinant mammalian cell (transient transfection), while in other recombinant mammalian cells the nucleic acid is integrated. Alternatively or in addition, the nucleic acid encoding a recombinant protein can be present in a plasmid and/or in a mammalian artificial chromosome (e.g., a human artificial chromosome). Alternatively or in addition, the nucleic acid can be introduced into the mammalian cell using a viral vector (e.g., a lentivirus, retrovirus, or adenovirus vector). The nucleic acid can be operably linked to a promoter sequence (e.g., a strong promoter, such as a β-actin promoter and CMV promoter, or an inducible promoter). A vector including the nucleic acid can, if desired, also include a selectable marker (e.g., a gene that confers hygromycin, puromycin, or neomycin resistance to the mammalian cell).

Liquid culture media (culture media) are known in the art. A liquid culture media can be supplemented with a mammalian serum (e.g., fetal calf serum and bovine serum), and/or a growth hormone or growth factor (e.g., insulin, transferrin, and epidermal growth factor). Any of the liquid culture media described herein can be selected from the group of animal-derived component free liquid culture medium, serum-free liquid culture medium, serum-containing liquid culture medium, chemically-defined liquid culture medium, and protein-free liquid culture medium. Non-limiting examples of chemically-defined liquid culture media, animal-derived component free liquid culture media, serum-free liquid culture media, and serum-containing liquid culture media are commercially available.

A liquid culture medium typically includes an energy source (e.g., a carbohydrate, such as glucose), essential amino acids (e.g., the basic set of twenty amino acids plus cysteine), vitamins and/or other organic compounds required at low concentrations, free fatty acids, and/or trace elements. The liquid culture media (e.g., a first and/or second liquid culture medium) can, if desired, be supplemented with, e.g., a mammalian hormone or growth factor (e.g., insulin, transferrin, or epidermal growth factor), salts and buffers (e.g., calcium, magnesium, and phosphate salts), nucleosides and bases (e.g., adenosine, thymidine, and hypoxanthine), protein and tissue hydrolysates, and/or any combination of these additives.

A wide variety of different liquid culture media that can be used to culture cells (e.g., mammalian cells) in any steps of any of the methods described herein are known in the art. Medium components that also may be useful in the present processes include, but are not limited to, chemically-defined (CD) hydrolysates, e.g., CD peptone, CD polypeptides (two or more amino acids), and CD growth factors. Additional examples of liquid tissue culture medium and medium components are known in the art.

Liquid culture medium obtained from a recombinant mammalian cell culture can be filtered or clarified to obtain a liquid culture medium that is substantially free of cells and/or viruses. Methods for filtering or clarifying a liquid culture medium in order to remove cells are known in the art (e.g., 0.2-μm filtration, filtration using an Alternating Tangential Flow (ATF™) system, a tangential flow filtration (TFF) system, or any of the systems described in U.S. Provisional Patent Application No. 61/878,502). Recombinant cells can also be removed from liquid culture medium using centrifugation and removing the supernatant that is liquid culture medium that is substantially free of cells, or by allowing the cells to settle to the gravitational bottom of a container (e.g., vessel) containing the liquid culture medium, and removing the liquid culture medium (the liquid culture medium that is substantially free of cells) that is distant from the settled recombinant mammalian cells. In some embodiments, the one or more (e.g., two, three, or all) of the first culture medium, the second culture medium, the third culture medium, and the fourth culture medium are identical.

The liquid culture medium used in any of the steps in any of the methods described herein can be any of the types of liquid culture medium described herein or known in the art. In any of the exemplary methods for isolating a recombinant protein described herein, a liquid culture medium obtained from a production cell culture can be diluted by addition of a second fluid (e.g., a buffer).

The liquid culture medium containing a recombinant protein (e.g., a recombinant therapeutic protein) that is substantially free of cells can be stored (e.g., at a temperature below about 15° C. (e.g., below about 10° C., below about 4° C., below about 0° C., below about −20° C., below about −50° C., below about −70° C., or below about −80° C.) for at least 1 day (e.g., at least about 2 days, at least about 5 days, at least about 10 days, at least about 15 days, at least about 20 days, or at least about 30 days) prior to isolating the recombinant protein (e.g., prior to feeding the liquid culture medium into the first MCCS (e.g., first PCCS)). Alternatively, in some examples the liquid culture medium containing a recombinant protein that is substantially free of cells is fed into a system used to isolate the recombinant protein.

A recombinant protein can be a recombinant therapeutic protein. Non-limiting examples of recombinant therapeutic proteins that can be produced by the methods provided herein include immunoglobulins (including light and heavy chain immunoglobulins, antibodies, or antibody fragments (e.g., any of the antibody fragments described herein), enzymes (e.g., a galactosidase (e.g., an alpha-galactosidase), Myozyme®, or Cerezyme®), proteins (e.g., human erythropoietin, tumor necrosis factor (TNF), or an interferon alpha or beta), or immunogenic or antigenic proteins or protein fragments (e.g., proteins for use in a vaccine). The recombinant therapeutic protein can be an engineered antigen-binding polypeptide that contains at least one multifunctional recombinant protein scaffold (see, e.g., the recombinant antigen-binding proteins described in Gebauer et al., Current Opin. Chem. Biol. 13:245-255, 2009; and U.S. Patent Application Publication No. 2012/0164066 (herein incorporated by reference in its entirety)). Non-limiting examples of recombinant therapeutic proteins that are antibodies include: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, amatuximab, anatumomab, anrukinzumab, apolizumab, arcitumomab, atinumab, tocilizumab, basilizimab, bectumomab, belimumab, bevacizumab, besilesomab, bezlotoxumab, biciromab, canakinumab, certolizumab, cetuximab, cixutumumab, daclizumab, denosumab, densumab, eculizumab, edrecolomab, efalizumab, efungumab, epratuzumab, ertumaxomab, etaracizumab, figitumumab, golimumab, ibritumomab tiuxetan, igovomab, imgatuzumab, infliximab, inolimomab, inotuzumab, labetuzumab, lebrikizumab, moxetumomab, natalizumab, obinutuzumab, oregovomab, palivizumab, panitumumab, pertuzumab, ranibizumab, rituximab, tocilizumab, tositumomab, tralokinumab, tucotuzumab, trastuzumab, veltuzumab, zalutumumab, and zatuximab. Additional examples of recombinant therapeutic antibodies that can be produced by the methods described herein are known in the art. Additional non-limiting examples of recombinant therapeutic proteins that can be produced by the present methods include: alglucosidase alfa, laronidase, abatacept, galsulfase, lutropin alfa, antihemophilic factor, agalsidase beta, interferon beta-la, darbepoetin alfa, tenecteplase, etanercept, coagulation factor IX, follicle stimulating hormone, interferon beta-la, imiglucerase, dornase alfa, epoetin alfa, insulin or insulin analogs, mecasermin, factor VIII, factor VIIa, anti-thrombin III, protein C, human albumin, erythropoietin, granulocyte colony stimulating factor, granulocyte macrophage colony stimulating factor, interleukin-11, laronidase, idursuphase, galsulphase, α-1-proteinase inhibitor, lactase, adenosine deaminase, tissue plasminogen activator, thyrotropin alpha (e.g., Thyrogen®) and alteplase. Additional examples of recombinant proteins that can be produced by the present methods include acid α-glucosidase, alglucosidase alpha (e.g., Myozyme® and Lumizyme®), α-L-iduronidase (e.g., Aldurazyme®), iduronate sulfatase, heparan N-sulfatase, galactose-6-sulfatase, acid β-galactosidase, β-glucoronidase, N-acetylglucosamine-1-phosphotransferase, α-N-acetylgalactosaminidase, acid lipase, lysosomal acid ceramidase, acid sphingomyelinase, β-glucosidase (e.g., Cerezyme® and Ceredase®), galactosylceramidase, α-galactosidase-A (e.g., Fabrazyme®), acid β-galactosidase, β-galactosidase, neuraminidase, hexosaminidase A, and hexosaminidase B.

A secreted, soluble recombinant protein can be recovered from the liquid culture medium by removing or otherwise physically separating the liquid culture medium from the cells (e.g., mammalian cells). A variety of different methods for removing liquid culture medium from cells (e.g., mammalian cells) are known in the art, including, for example, centrifugation, filtration, pipetting, and/or aspiration. The secreted recombinant therapeutic protein can then be recovered and isolated from the liquid culture medium using a variety of biochemical techniques including various types of chromatography (e.g., affinity chromatography, molecular sieve chromatography, cation exchange chromatography, hydrophobic interaction chromatography, or anion exchange chromatography) and/or filtration (e.g., molecular weight cut-off filtration).

The fluid can be removed from the sterile process vessel by continuous or periodic removal. In some examples, the fluid removed from the sterile process vessel comprises a recombinant protein. In some examples, the fluid removed from the sterile process vessel comprises a culture medium. In some examples, the fluid removed from the sterile process vessel does not comprise a recombinant protein.

EXAMPLES

The invention is further described in the following example, which do not limit the scope of the invention described in the claims.

Example 1

Figure 2:
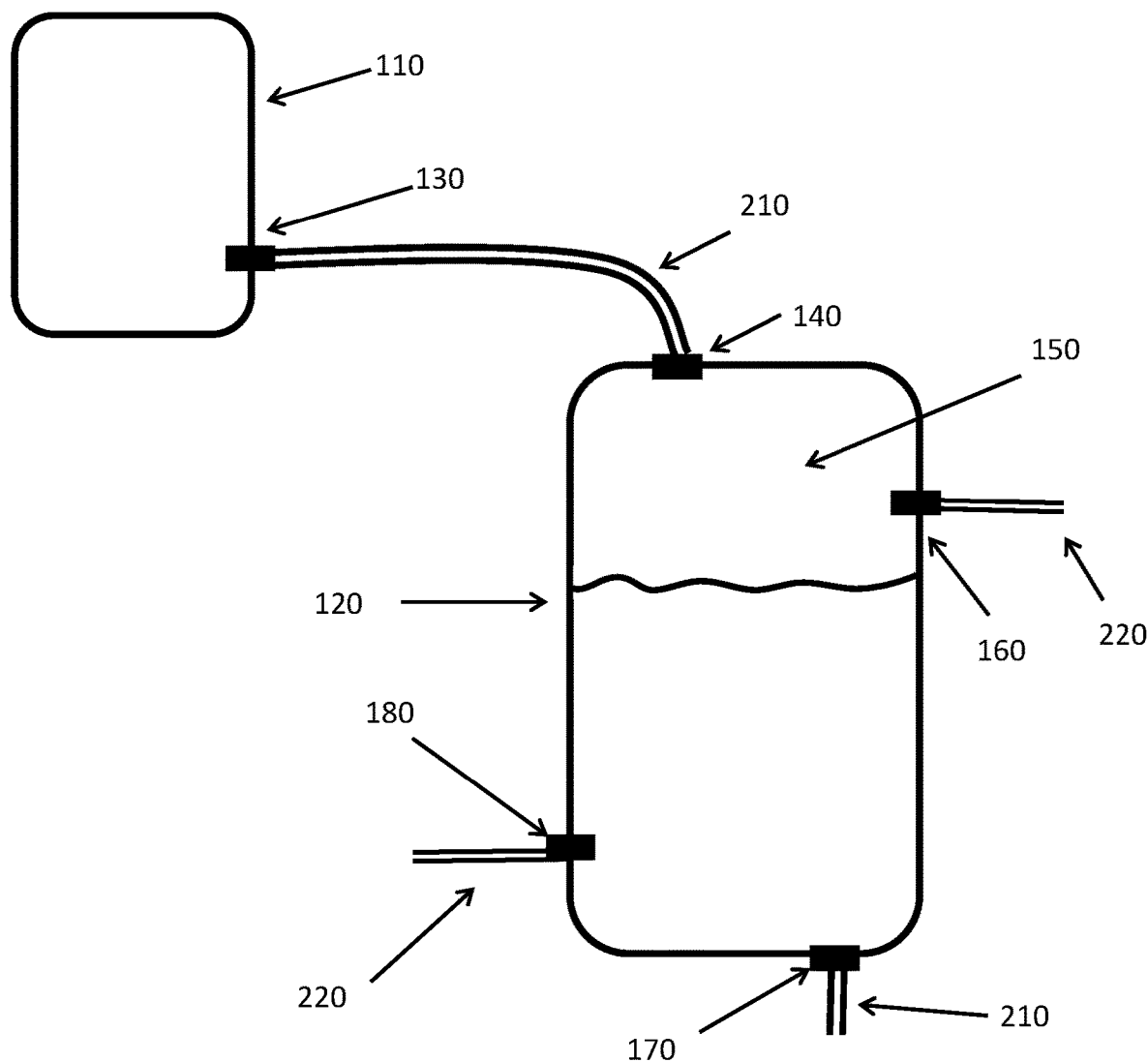
FIG. 2 is a schematic diagram illustrating an example system for isolating sterile process streams from non-sterile environments according to the present invention.

FIG. 2 describes an example system for isolating sterile process streams from non-sterile environments according to the present invention. The system can be any sterile process, including, for example a component of a biological manufacturing process stream. As demonstrated in FIG. 2, the system comprises a sterile process vessel (110) (e.g., a first vessel) comprising a fluid outlet (130). For a biological manufacturing process stream, the first vessel can be, for example, a fluid conduit for flowing liquid media, a bioreactor (e.g., any of the exemplary bioreactors described herein or known in the art), one or more components of chromatography systems (e.g., a chromatography column), one or more components of microfiltration system, one or more components of an ultrafiltration/diafiltration system. The system described in FIG. 2 further comprises an isolation vessel (120) (e.g., a second vessel) comprising a fluid inlet (140) in fluid communication via a fluid conduit (210) with the fluid outlet (130) of the first vessel (110) and configured such that fluid entering the second vessel passes through a sterilizing-gas filled head space (150) within the second vessel (120), a fluid outlet (170) configured such that fluid exiting second vessel is removed from below the sterilizing gas-filled headspace (150) within the second vessel (120). The second vessel includes at least one gas inlet (180) to supply a sterilizing gas via a gas conduit (220) to fill the headspace of the second vessel. The second vessel also includes at least one gas outlet (160) configured to continuously or periodically vent gas from the isolation.

FIG. 1 provides an exemplary embodiment for isolating sterile process streams from non-sterile environments according to the present invention. For the system described in FIG. 1, waste streams from a sterile process vessel (e.g., a first vessel, not shown) are in fluid communication with an isolation vessel (e.g., a second vessel), the isolation vessel configured such that fluid enters the top of the second vessel and passing through a sterilizing-gas filled head space within the second vessel. The second vessel further comprising a fluid outlet configured such that fluid exiting second vessel is removed from below the sterilizing gas-filled headspace (i.e., below the fluid filled portion of the second vessel) within the second vessel. FIG. 2 further demonstrates a pump system comprising a pump configured to remove a volume of fluid from the second vessel outlet and flow the volume into a receptacle for disposing of a biological waste stream. The second vessel includes at least one gas inlet in gas communication with system for generating or delivering a sterilizing gas, or for generating and delivering a sterilizing gas (e.g., an ozone generating system) to fill the headspace of the second vessel. According to this embodiment, the sterilizing gas is sparged into the second vessel. The second vessel also includes at least one gas outlet configured to continuously or periodically vent gas from the isolation.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of decreasing contamination of a sterilized biological manufacturing system, the method comprising:
   (a) providing a sterilized biological manufacturing system and an isolation vessel, wherein:
   the sterilized biological manufacturing system comprises a liquid comprising a recombinant therapeutic protein;
   the isolation vessel comprises a headspace of ozone and a liquid; and
   the sterilized biological manufacturing system comprises a fluid outlet in fluid communication with a fluid inlet of the isolation vessel; and
   (b) continuously flowing a first volume of the liquid out of the fluid outlet of the sterilized biological manufacturing system, into the fluid inlet of the isolation vessel, and through the headspace of the isolation vessel, wherein:
   the sterilized biological manufacturing system is a bioreactor, a chromatography system, a microfiltration (MF) system, or an ultrafiltration/diafiltration (UF/DF) system; and
   ozone is sparged into the isolation vessel or introduced directly into the headspace of the isolation vessel; and
   the concentration of ozone is controlled within the headspace of the isolation vessel to provide a sterilizing atmosphere.

2. The method of claim 1, wherein the isolation vessel further comprises:
   (i) a fluid outlet configured such that the liquid exiting the isolation vessel is flowed from below the headspace;
   (ii) at least one gas inlet; and
   (iii) at least one gas outlet.

3. The method of claim 1, wherein the liquid in the sterilized biological manufacturing system comprises a cell comprising the recombinant therapeutic protein.

4. The method of claim 1, wherein the fluid outlet of the sterilized biological manufacturing system is connected to the fluid inlet of the isolation vessel by a fluid conduit.

5. The method of claim 2, wherein the sterilized biological manufacturing system comprises a pump in fluid communication with the fluid outlet of the sterilized biological manufacturing system, a pump in fluid communication with the fluid outlet of the isolation vessel, or both.

6. The method of claim 2, wherein the at least one gas outlet is configured to continuously or periodically vent gas from the isolation vessel.

7. The method of claim 2, wherein the at least one gas outlet is in gas communication with an ozone destruction unit.

8. The method of claim 1, wherein the sterilized biological manufacturing system comprises a dissolved gas probe or a sensor for monitoring the concentration of ozone gas within the headspace of the isolation vessel.

* * * * *